US00PP25285P3

(12) United States Plant Patent
Noodelijk

(10) Patent No.: US PP25,285 P3
(45) Date of Patent: Feb. 10, 2015

(54) *CELOSIA* PLANT NAMED 'TWISTED'

(50) Latin Name: *Celosia argentea*
Varietal Denomination: Twisted

(71) Applicant: Floritec Breeding, B.V., Amsterdam (NL)

(72) Inventor: Robert Noodelijk, Woubrugge (NL)

(73) Assignee: Floritec Breedings, B.V., Amsterdam (NL)

( * ) Notice: Subject to any disclaimer, the term of this patent is extended or adjusted under 35 U.S.C. 154(b) by 128 days.

(21) Appl. No.: 13/815,400

(22) Filed: Feb. 28, 2013

(65) Prior Publication Data

US 2013/0247261 P1 Sep. 19, 2013

(30) Foreign Application Priority Data

Mar. 16, 2012 (QZ) ..... PBR 20120636

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Kent L Bell
(74) *Attorney, Agent, or Firm* — Jondle & Associates P.C.

(57) ABSTRACT

A new and distict variety of *Celosia* plant named 'Twisted' particularly characterized by having many red-purple colored crested inflorescences, multiple crests per branch, prolific branching, and a compact, symmetrical plant habit is disclosed.

3 Drawing Sheets

Genus and species: *Celosia argentea.*
Variety denomination: 'Twisted'.

CROSS REFERENCE TO RELATED APPLICATIONS

This application claims the benefit of priority from EU Community Plant Variety Rights (CPVR) application no. 20120636, filed Mar. 16, 2012, which is incorporated herein by reference in its entirety.

BACKGROUND OF THE NEW PLANT

The present invention comprises a new and distinct variety of *Celosia* plant, botanically known as *Celosia argentea* and hereinafter referred to by the variety name 'Twisted'. The breeding and selection objective for 'Twisted' was to create new indoor *Celosia* cultivars with a compact, freely branching plant habit that could be propagated by vegetative cuttings. 'Twisted' is the result of an open pollination conducted in a greenhouse in May 2009 in Monster, The Netherlands among groups of un-named and unpatented *Celosia* plants, and grown under the control of the inventor for breeding purposes. A single plant was selected by the inventor in March 2010 for further evaluation and asexual propagation.

'Twisted' was first asexually propagated via vegetative cuttings in Monster, The Netherlands in July 2010 and has been asexually reproduced by vegetative cuttings in Monster, The Netherlands for approximately one and a half years. The new cultivar has been found to retain its distinctive characteristics through successive asexual propagations via vegetative cuttings.

European Union Community Plant Variety Rights for this variety were applied for on Mar. 16, 2012. 'Twisted' has not been sold or made publicly available anywhere in the world more than one year prior to the filing date of this application.

SUMMARY OF THE NEW PLANT

The following are the most outstanding and distinguishing characteristics of the new variety when grown under normal horticultural practices in Monster, The Netherlands.

1. Red-purple colored crested inflorescences;
2. Multiple crests per branch;
3. Prolific branching; and
4. Compact, symmetrical plant habit.

DESCRIPTION OF THE PHOTOGRAPHS

This new *Celosia* plant is illustrated by the accompanying photographs; the colors shown are true as can be reasonably obtained by conventional photographic procedures. The photographs are of plants that have been in bloom for approximately three weeks.

DESCRIPTION OF THE NEW PLANT

Figure 1:
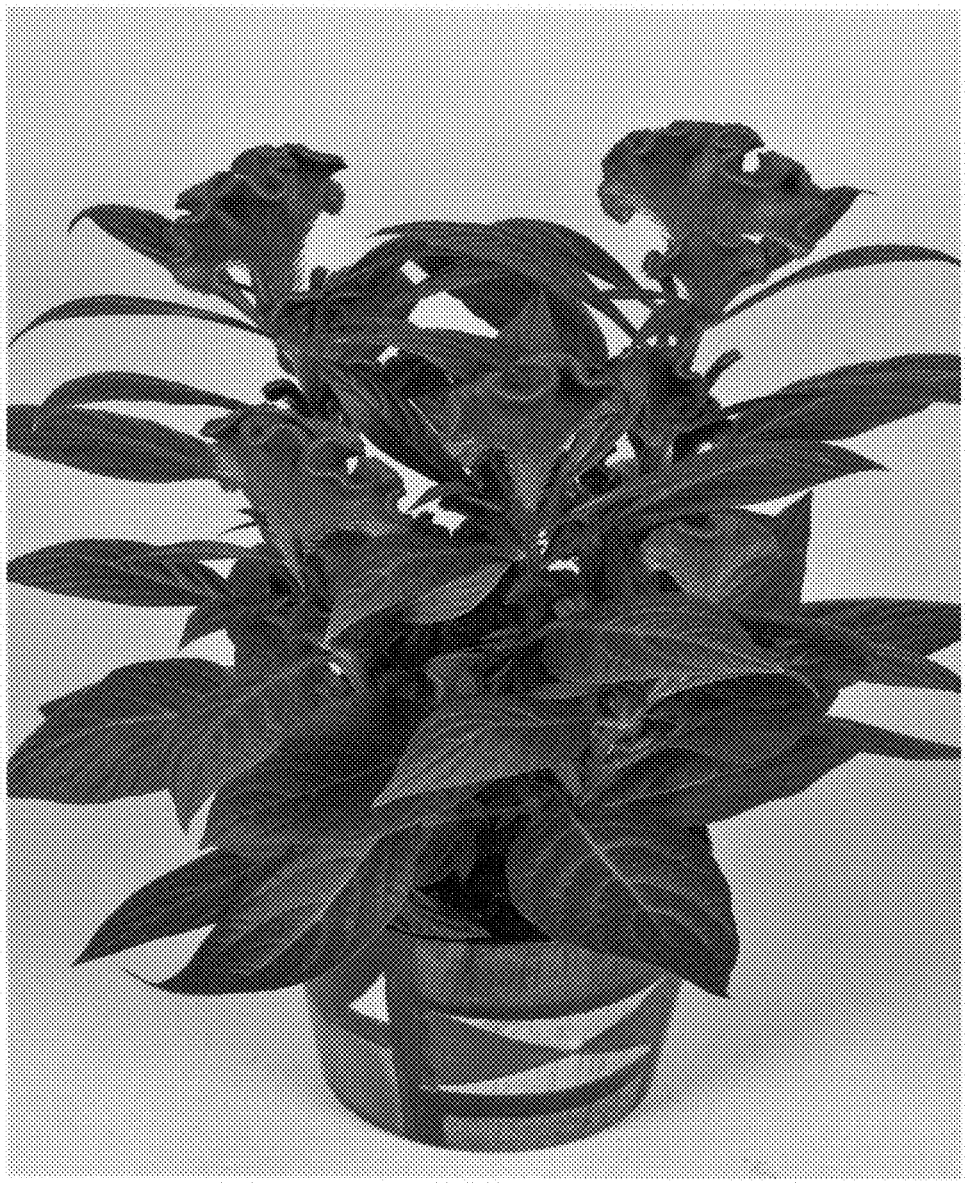
FIG. 1 shows a plant in full bloom.
Figure 2:
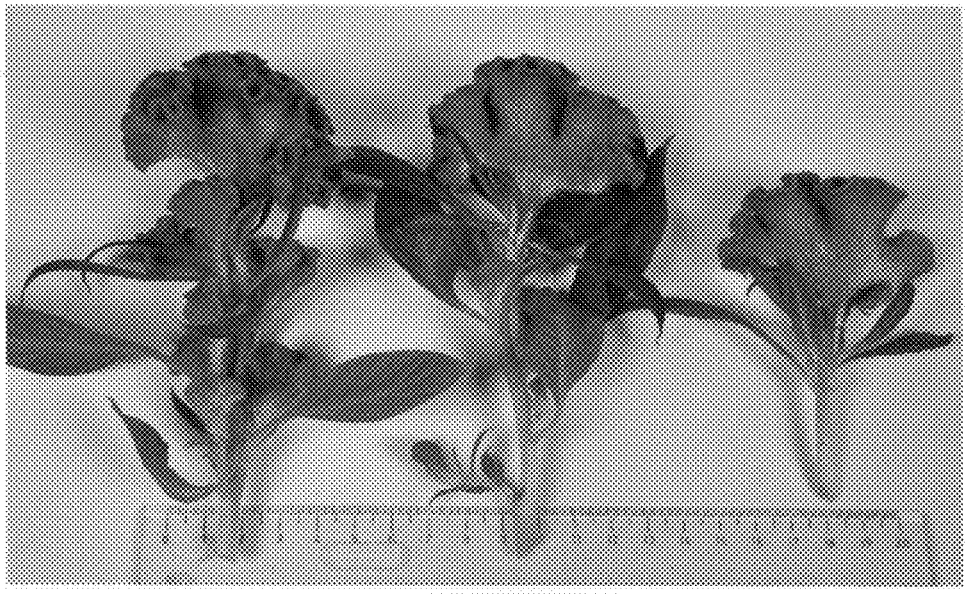
FIG. 2 shows a close-up of the individual crests and inflorescence per branch.
Figure 3:
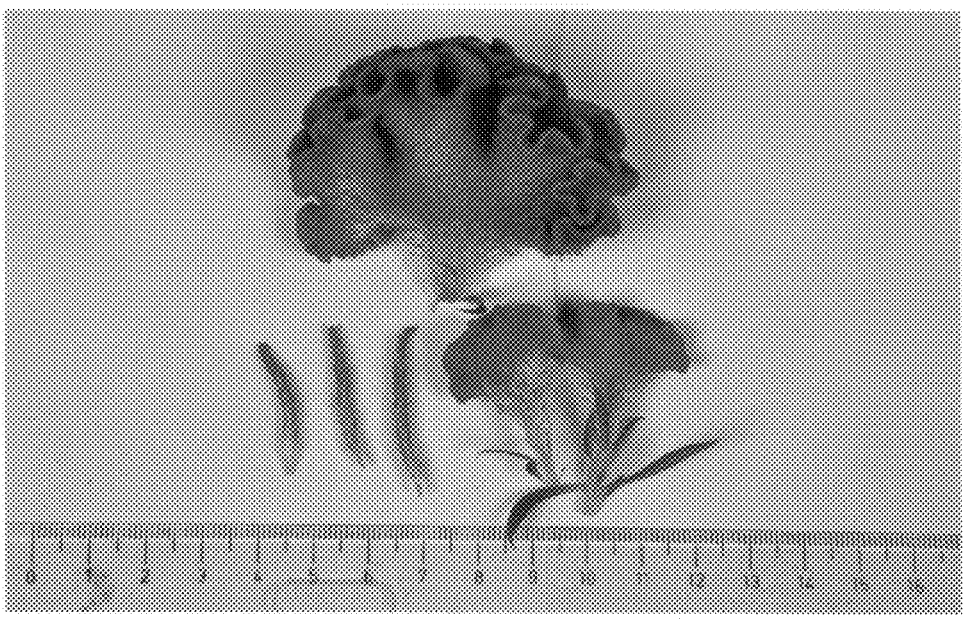
FIG. 3 shows a close-up of larger and smaller crests and needle forms.
Figure 4:
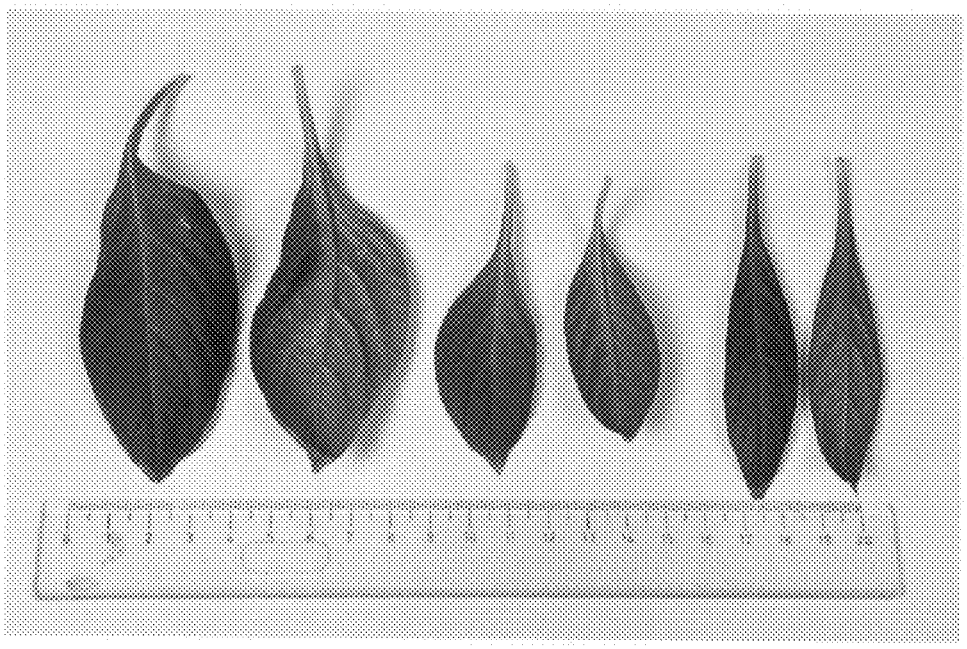
FIG. 4 shows a close-up of the upper and lower surfaces of the leaves.

The following detailed description sets forth the distinctive characteristics of 'Twisted'. The data which define these characteristics was collected from asexual reproductions carried out in Monster, The Netherlands. The plant history was taken on 8-week old plants planted in week 31 of 2011 and grown indoors in Monster, The Netherlands under controlled day length and temperature conditions. Color references are primarily to The R.H.S. Colour Chart of The Royal Horticultural Society of London (R.H.S.) (1995 edition).

DETAILED BOTANICAL DESCRIPTION OF THE NEW PLANT

Plant:

*Shape*.—Rounded.

*Growth habit*.—Spreading.

*Growth rate*.—Fast.

*Response time*.—7 to 8 weeks.

*Performance of the plant* (*shelf life*).—10 weeks.

*Height*.—25.0 cm to 30.0 cm (with weekly growth retardant).

*Width*.—15.0 cm to 20.0 cm (with weekly growth retardant).

*Tonality from distance*.—A very rich flowering compact *Celosia* pot plant.

Branches:

*Stem*.—Color: RHS 145C (Green). Strength: Strong. Brittleness: Not brittle. Anthocyanin coloration: Absent.

*Length of lateral branch* (*from top to bottom*).—9.0 cm to 18.0 cm.

*Diameter of lateral branch*.—0.5 cm.

*Lateral branch color*.—RHS 145C (Green).

*Lateral branch attachment*.—Petiolate.

*Branching* (*average number of lateral branches*).—Prolific with 4 to 6 breaks after pinching.

*Auxiliary branch* (*when present*).—Length: Approximately 1.0 cm. Diameter: 0.2 cm. Color: RHS 147C (Green).

Leaves:

*Color*.—Upper surface: RHS 137B (Green). Lower surface: RHS 147C (Green).

*Venation*.—Color: RHS 147C (Green). Pattern: Pinnate.

*Size*.—General: Medium, the youngest foliage is small. Length: 5.0 cm (youngest) to 11.0 cm (oldest). Width: 0.5 cm (youngest) to 5.5 cm (oldest).

*Quantity* (*number per lateral branch from base to tip*) .—4 to 10.

*Shape*.—Cordiform.

*Apex*.—Acute.

*Base*.—Attenuate.

*Margin*.—Entire.

*Texture* (*both surfaces*).—Leathery.

Inflorescence:

*Type*.—Fasciation at the tips of the majority of branches results in a colored crest that differs in size and form. Fasciation of the lateral branches results in large crests. Fasciation, when present on the auxiliary branches, results in much smaller crests or into a needle form, all with a hairy surface.

*Size of crest of the lateral branch*.—1 week old crest: Bow width: 5.0 cm to 7.0 cm. Width of curled edge: 3.0 cm. 3 week old crest: Bow width: 7.0 cm to 10.0 cm. Width of curled edge: 4.0 cm to 5.0 cm.

*Size of crest of auxiliary branch* (*when present, no development of crest*).—Bow width: 2.0 cm to 3.0 cm. Width of curled edge: 0.5 cm.

*Size of needles of auxiliary branch* (*when present, no development of crest*).—Length: 2.0 cm to 3.0 cm. Diameter: 0.3 cm.

*Number of crests per lateral branch from top to bottom*.—4 to 8.

*Color of the crests*.—Mainly RHS 61A (Red-purple) with occasionally a tiny RHS 45B (Red) line on the outer edge.

*Number of blooms per crest*.—Usually 'Twisted' is sterile, occasionally some blooms appear at the bottom of the crests or randomly at the surface of the crest.

*Number of crests when present*.—1 to 20.

*Fragrance*.—Absent.

*Discoloration to color*.—Absent.

Ray florets (when present):

*Texture* (*both upper and lowers surfaces*).—Papery.

*Number*.—5.

*Cross-section*.—Flat.

*Longitudinal axis of majority*.—Straight.

*Apex*.—Acuminate.

*Margin*.—Entire.

*Length*.—0.5 cm.

*Width*.—0.3 cm.

*Length to width ratio*.—Medium.

*Color*.—Upper surface of the outer ray florets: RHS 61A (Red-purple). Lower surface of the ray-florets: RHS 61A (Red-purple).

Reproductive organs:

*Stamen*.—Length: Very thin, 0.05 cm. Color: RHS 61A (Red-purple).

*Pollen*.—Amount: Present, moderate. Color: RHS 155A (White).

*Style*.—Appearance: Very thin. Color: RHS 61A (Red-purple). Length: 0.6 cm.

*Stigma*.—Color: RHS 61A (Red-purple). Width: 0.1 cm.

Fruit/seed set: Not observed.

Disease and pest resistance: Not tested.

Cold or drought tolerance: Not tested.

COMPARISON WITH COMMERCIAL CULTIVARS

'Twisted' differs from the commercial *Celosia* plant named 'Spitenz' (U.S. Plant Pat. No. 23,076) in that 'Twisted' has crested inflorescence with florets colored RHS 61A (red-purple), whereas 'Spitenz' has spiked inflorescence with florets colored RHS 78A (purple). Additionally, 'Twisted' has leaf venation colored RHS 147C (green), whereas 'Spitenz' has leaf venation colored RHS 45B (red).

I claim:

1. A new and distinct variety of *Celosia* plant named 'Twisted' as described and shown herein.

* * * * *